United States Patent [19]

Naumann et al.

[11] Patent Number: 5,660,998

[45] Date of Patent: Aug. 26, 1997

[54] METHOD FOR THE RAPID DETECTION OF MICROORGANISMS IN SAMPLES

[75] Inventors: Dieter Naumann; Harald Labischinski, both of Berlin, Germany

[73] Assignee: Bruker Analytik GmbH, Rheinstetten, Germany

[21] Appl. No.: 741,533

[22] PCT Filed: Feb. 8, 1990

[86] PCT No.: PCT/DE90/00081

§ 371 Date: Sep. 27, 1991

§ 102(e) Date: Sep. 27, 1991

[87] PCT Pub. No.: WO90/09453

PCT Pub. Date: Aug. 23, 1990

[30] Foreign Application Priority Data

Feb. 9, 1989 [DE] Germany ............... 39 03 777.0

[51] Int. Cl.[6] ............... C12Q 1/04; C12Q 1/24
[52] U.S. Cl. ............... 435/34; 435/30; 435/297
[58] Field of Search ............... 435/34, 4, 30, 435/294, 297; 356/442

[56] References Cited

U.S. PATENT DOCUMENTS

| 4,634,676 | 1/1987 | Sapatino | 435/294 |
| 5,061,621 | 10/1991 | Perlman | 435/30 |
| 5,112,745 | 5/1992 | Lorr | 435/38 |
| 5,137,812 | 8/1992 | Matner | 435/38 |

FOREIGN PATENT DOCUMENTS

| 0151855 | 8/1985 | European Pat. Off. . |
| 0164037 | 12/1985 | European Pat. Off. . |
| 490820 | 2/1976 | U.S.S.R. . |

OTHER PUBLICATIONS

Derwent's abstract Nr. 395 55 C/22, SU 690 069 publ. week 8022 No Date Avail.

Derwent's abstract Nr. 682 45X/36, SU 490 820, publ. week 36 No Date Avail.

Dickscheit: Handbuch der mikrobiologischen Laboratoriumstechnik, Publication Theodor Steinkopff, Dresden, 1967 pp. 107–121.

*Primary Examiner*—Ralph Gitomer

[57] ABSTRACT

The invention relates to a method for the rapid detection and enumeration of microorganisms. The spectroscopic detection is carried out, after brief incubation of the sample to be tested, by the detection of the growth of microcolonies, which is not yet detectable with the naked eye, on a solid culture plate following direct transfer of said microcolonies to a sample carrier by special impression techniques; the detection itself is carried out by recording the spectra of all, or of a representative number, of the impressions, using an IR microscope. It is not only possible to make statements with regard to the number of microorganisms in the sample but the high information content of the spectra can also be used for demanding microbiological differentiation work down to species identification.

2 Claims, 7 Drawing Sheets

METHOD FOR THE RAPID DETECTION OF MICROORGANISMS IN SAMPLES

The invention relates to a method for the rapid detection of microorganisms in a multiplicity of samples, such as, for example, urine, blood, water, foodstuffs, pharmaceutical raw materials and products, such as, for example, ointments, liquid preparations, etc., which as a rule should be free from such microorganisms or for which certain, specified limiting values for the total germ count or for individual, defined representatives of microorganisms should not be exceeded, as well as a device for carrying out the method.

Detection work of this type is carried out on a large scale in the clinical sector (sepsis, urinary tract infections, liquor testing) and non-clinical sector (assessment of the freedom from germs or the contamination of starting materials and end products, such as, for example, water, milk, foodstuffs, etc.), since the results of such tests are of great clinical significance but also of great significance for quality control, stability assessment and other product and production method tests, for example in industrial sectors. Because of the frequent possibility of exponential growth of the microorganisms to be detected and of the very early detection of, for example, infections, which is often necessary in the clinical sector to instigate therapeutic measures, for example in the case of life-threatening sepsis, or in the non-clinical sector, for example in the case of the production of pharmaceuticals, in order to reduce the unusability of entire batches, for example in the case of the use of contaminated starting materials, with possibly considerable economic consequences, a detection even of low germ counts (for example $<10^5$ per ml or g of sample) within as short as possible a time is required.

In the current state of the art, the methods used for carrying out detection tests are as a rule either methods which permit very rapid and highly specific detection of very small amounts of specific individual groups of microorganisms or methods which are able to detect a large variety of different microorganisms non-specifically, less rapidly and with comparatively distinctly larger amounts of microorganisms (approximately $>10^5$ bacteria per ml of test sample) (for a review compare, for example: Bergan, T. in: Methods in Microbiology, Vols. 14–16, London, Orlando, San Diego, San Francisco, New York, Toronto, Montreal, Sydney, Tokyo, Sao Paulo: Academic Press (1984); Kipps, T. J., Herzenberg, L. A., in: Habermehl, K.-O.: Rapid Methods and Automation in Microbiology and Immunology, Berlin, New York, Tokyo: Springer Verlag (1985); Toorova, T. P., Antonov, A. S., in: Colwell, R. R. and Grigorova, R.: Methods in Microbiology, Vol. 19, London, Orlando, San Diego, New York, Austin, Boston, Sydney, Tokyo, Toronto: Academic Press (1987); Thronsberry, C., in: Habermehl, K.-O.: Rapid Methods and Automation in Microbiology and Immunology, Berlin, New York, Tokyo: Springer Verlag (1985); Carlberg, D. M., in: Lorian, V.: Antibiotics in Laboratory Medicine, Baltimore, London, Los Angeles, Sydney: Williams & Wilkins (1986)). The first group includes in particular molecular-biological detection methods, with which the detection takes place indirectly by detection of a reaction of the sample, for example with monoclonal antibodies or also by DNA/DNA hybridization and similar techniques. A characteristic feature of these techniques is the necessity for the (expensive) production and preparation of highly specific reagents for each individual type of microorganism to be detected. It is, however, an advantage of these methods that a detection of the microorganisms at the same time already comprises an identification—accurate to a greater or lesser extent depending on the specificity of the reagents used—of the type of microorganism detected, insofar as cross-reactions with other types of organism, which are a frequent problem, can be disregarded. The use of these methods, which in any case is hardly routine to date, is therefore restricted for the foreseeable future to individual, particularly important (for example life-threatening germs in the case of an infection) groups of organisms. Representatives of the second group of methods typically include, for example, microcalorimetric, conductivity/impedance and optical measurements.

In the case of these methods the sample to be tested for the presence of microorganisms, for example bacteria, is as a rule placed in a suitable culture medium promoting the growth of the organisms and said medium is incubated under growth conditions which are as optimum as possible. Detection then takes place, for example, by detection of the heat production of the culture, using a microcalorimeter, or of the changes in the impedance of the culture liquid caused by the growth of the culture, using suitable conductivity measurement systems. In the broader sense, this group of methods also includes simple optical measurements of the turbidity of the culture medium or the light-optical detection of microorganisms. The advantage of this group of methods lies in the relatively universal application to very many groups of organisms and, with the exception of the last mentioned method variant, in the fact that said methods can be operated and automated relatively simply. A disadvantage, on the other hand, is the lack of a possibility for parallel identification of the microorganisms, which, if necessary, must be carried out separately using other methods, and also the relatively long period, caused inter alia by the culture, between sample introduction and detection and the comparatively high detection limits (for example about $10^5$ cells/ml of urine in the case of the urological samples which are particularly frequent in medical practice).

DE-A1-32 47 891 describes a method for the identification of microorganisms on the basis of image-analytical evaluation of infra-red spectra in selected, small wavenumber regions (compare also Giesbrecht, P., Naumann, D., Labischinski, H., in: Habermehl: Methods and Automation in Microbiology and Immunology, pp. 198–206, Berlin, Springer Verlag (1985); Naumann, D., Fijala, V., Labischinski, H., Giesbrecht, P., J. Mol. Struct. 174, 165–170 (1988)). Despite powerful infra-red spectroscopes and infra-red microscopes, the sensitivity of these methods is not sufficient to enable samples to be investigated for the presence of microorganisms.

Now, it is the object of the present invention to develop a method for the rapid detection of a very small number of microorganisms of the above-mentioned type and to provide the possibility for rapid and reliable detection of very diverse microorganisms, even if the number of microorganisms in the sample to be tested is very small.

This object is achieved according to the invention by applying a sample of microorganisms to an essentially solid culture carrier, in a dilution that enables the growth of the microorganisms into locally separated colonies, initiating a short-term growth of the microorganisms of at least six generation times, transferring regions of the surface of the culture carrier on which microcolonies are present so as to maintain their relative distances from each other to an optical carrier that is either at least partially transparent or reflective in the desired spectral region, carrying out directly the transfer of the microorganisms from the culture carrier onto a stamp, the stamp surface of which consists of a material that is transparent or reflective in the desired wave range, locating individual colonies of the transferred microorganisms under an infrared (IR) microscope, and sequentially recording and evaluating individually the IR spectra of the transferred microorganism colonies by means of the IR microscope in the transmission or reflection mode, preferably using apertures in the diameter range of about 10–200 µm. The invention enables the advantages of the various groups of methods employed hitherto, that is to say detection of low germ counts of microorganisms, possibility for combination with identification methods, short time requirement and broad applicability to as far as possible all types of organisms in accordance with a uniform method which is easy to automate, to be achieved in combination in a single method. At the same time, the method according to the invention can also be employed effectively in routine operation in microbiological laboratory practice. The spatially separated growth of microcolonies, starting from single individuals of the microorganisms directly from the sample to be tested, on the culture carrier and the examination of a surface sample, obtained from the culture carrier, after locality-true transfer, makes the method according to the invention suitable and valuable specifically for the examination of samples which per se should be free from microorganisms or which have only a very low germ count.

The growth period of at least 6 generation times of the organisms to be detected, which is provided according to the invention, is based on the consideration that a locality-bound concentration of the particular microorganism on a solid carrier for the sample, in particular on an agar plate, represents an enrichment of the microorganism to a degree such that the colonies formed are sufficiently large for detection using a microscope, in particular an IR microscope and an IR spectroscope. As a result of the low concentration of the microorganisms in the sample to be tested, if necessary after a possible dilution, it is ensured that the individual microorganisms are applied to the surface of the solid carrier as individuals with a spatial separation which is so large that the colonies of microorganisms formed therefrom do not mutually impair one another. In this way, a pure culture of the microorganisms in the microscopic range is carried out directly from the sample, without a prior or subsequent isolation of the individual microorganism being required. The size of the colonies of the microorganisms should be such that the particular colony has a superficial extent which corresponds to a number of at least about 50 individuals, for example bacteria. Starting from a single cell, $2^6$, or 64, cells are formed in 6 generation times, the superficial extent of which cells already suffices for infra-red spectroscopy. In the case of particularly large cells, smaller numbers of cells, such as $2^5$, can also be sufficient. For safety reasons, however, the procedure is as a rule carried out using a larger superficial extent of the colony, which is achieved, in particular, by at least 7–12 generation times. 10 generation times correspond to about 1000 cells.

The time period within which the colony growth is achieved depends on the growth rate of the individual microorganisms. Usually, a generation time of 20–40 minutes suffices for samples which are taken from the clinical sector and a generation time of about one hour for water samples. In order to be sure, the period is kept at about 4–10 hours in practice. The period which is required and suitable in a particular case can also be determined by preliminary experiments. The result of this is that in the case of routine use of the method it is possible to work with the shortest possible period in order to obtain the desired result as rapidly as possible. As a result of the locality-true transfer of surface layers of the resulting microcolonies to the optical carrier, mixing of constituents of different colonies is avoided. This makes the method according to the invention also suitable for the enumeration and identification of the microorganisms. A high optical resolution and highly meaningful results are achieved by the use of apertures of suitable diameter.

A particularly suitable device for carrying out the method according to the invention is disclosed herein. Advantageous further developments and features of the method according to the invention and of the device will become apparent from the description which follows. The individual features may be implemented individually or in any desired combination of several or all of them.

The preferred use of infra-red microscopes, which, as a result of the further development of the measurement techniques for Fourier transform infra-red spectroscopy, enable sample amounts of down to below the nanogram range to be measured reproducibly, is particularly advantageous. As a result of the newly developed techniques for sample transfer of micro-colonies of the microorganisms without prior pure culture, in particular directly onto infra-red-transparent or reflective carrier materials, which can be measured directly in the optical and infra-red-spectroscopic mode of the IR microscope, a particularly rapid and reliable detection is facilitated. Surprisingly, the detection is successful even in the case of the preferred use of one or more even very small sections (for example only a few 100 wavenumbers) from the total spectrum, so that it is also possible to use carrier materials which are IR-transparent or reflect well only in very small wavenumber ranges. A procedure which proved particularly advantageous for rapid detection was the use of a stamp impression method for sample transfer from a culture carrier customarily used in bacteriology, in particular an agar culture plate, according to which method, in particular, a stamp, for example a circular stamp, of IR-transparent material of suitable thickness is pressed briefly (for example for less than 1 second) onto the culture plate—in an appropriate manner using a guide, or optionally also directly by hand—and lifted off again, whereby parts of the microcolonies of the —maybe even different— microorganisms which (after brief incubation of, for example, a Urine sample) are present on the culture plate and which as a rule are not yet detectable with the naked eye, can be transferred locality-true to the stamp plate, so that the impression samples on the stamp plate can be measured directly, without further preparation effort, on the sample stage of the FT-IR microscope. This procedure offers the additional advantage that, at the wish of the operator, the incubation of the original culture plates can be continued for subsequent monitoring purposes. The transfer to the stamp used as optical carrier can also be effected by pressing the movable culture carrier against the stamp surface.

An additional advantage has been found to reside in the fact that the microscope, in particular the light-optical mode of a preferentially used IR microscope (if appropriate supported by methods for image evaluation using, for example, an attached television camera with or without further image processing facilities), can, if desired, also be used not only to drive the regions of the stamp which are of interest but also for pre-evaluation of the sample (for example according to the morphology of the microcolonies, color and shape of the microorganisms (cocci, rods, etc.)). The actual, reliable detection is then carried out by recording the corresponding infra-red spectra, which, because of the fundamental chemical composition common to all microorganisms (cell wall, membrane, protein, ribosomes, nucleic acids, etc.), in principle have similar spectral characteristics for all possible microorganisms, so that the method, as desired, can be used for practically all microorganisms without limitation. A particular advantage of the method proves to be the fact that the IR-spectra of micro-organisms, irrespective of the fact that they are similar in principle as a consequence of the specific chemical composition of the cells of individual types of microorganisms, if desired also permit, without further expenditure on equipment, a differentiation and identification of microorganisms measured to be carried out by comparison of the spectra with those of a suitable reference database, and this down to the sub-species level, using a procedure described earlier (Giesbrecht, P., Naumann, D., Labischinski, H., in: Habermehl: Methods and Automation in Microbiology and Immunology, pp. 198–206, Berlin: Springer Verlag (1985); Naumann, D., Fijala, V., Labischinski, H., Giesbrecht, P., J. Mol. Struct. 174, 165–170 (1988)), to which reference is made here.

According to the invention it is possible, as already mentioned, to carry out an identification of microorganisms in addition to the detection. The device according to the invention can, however, advantageously be designed such that all three main tasks, for example detection, identification and where appropriate even sensitivity tests, can be carried out, so that an old aim—which, however, it is not possible to achieve with the state of the art to date—of a uniform technique with a procedure which is uniform in principle can now be achieved for any desired microorganisms. In this context, it proves to be highly advantageous fully to automate the entire procedure, from sample preparation via sample measurement to output of the result, if desired even including a subsequent further processing of the result, say in the sense of an identification or sensitivity test, since the method can in principle be carried out in a uniform manner for all microorganisms under consideration and the technique of recording spectra using the FT-IR microscope technique provides from the outset a measurement result which is digital and thus easy to process by electronic means.

When carrying out a preferred embodiment of the method according to the invention, the sample to be tested, such as, for example, urine, blood, liquor, water, aqueous extracts from foodstuffs, ointments, medicaments and the like, is coated in the manner customary in microbiology onto a solid culture plate in the manner known from microbiology in a dilution such that the microorganisms which may be present in the sample Grow individually into colonies. After a short culture time of about 4–10 hours (depending on the type of sample and the Generation time of the microorganisms to be detected), in which microcolonies which consist, for example, of about $10^3$ organisms and are not yet detectable with the naked eye have formed on the plate, the transfer from the culture plate to the carrier, which is transparent or reflective in the desired wavenumber range, is effected, for example by placing a sample carrier disc, which is, for example, about 2 mm thick and 3 cm in diameter and is made, for example, of ZnSe, polished steel or the like, on the plate and then lifting it off again, so that a locality-consistent impression of adhering microorganisms from the culture plate is obtained on the sample carrier. The sample carrier is then transferred manually or under automated control to the sample stage of the microscope, in particular an IR microscope. At this point in the method, several variants are possible depending on the wishes of the person carrying out the experiment and the given detailed features of the microscope. In the simplest case, the sample plate can be manually/visually inspected using the optical mode of the microscope. An initial estimate of the germ count present in the sample can already be made from the number of optically discernible microcolonies (taking into account any dilution factors depending on the sample dilution in the manner customary in microbiology) and, if appropriate, a rough estimate can also already be made from the colony morphology (size, color, surface nature etc.) with regard to possibly different groups of organisms. If no microcolonies are detectable at this point, the method can already be concluded at this point as having a "negative" result. The actual detection is then carried out using the infra-red-spectroscopic mode of the microscope, in which the infrared spectra of the corresponding microcolonies are recorded successively, with the aid of the aperture system—which is an integral feature of every IR microscope—for all, or for a representative number of, the microcolonies present on the sample carrier. Of the microcolony impressions previously detected optically, only those which have spectra which are compatible with the chemical composition typical for microorganisms (in particular proteins, lipids, nucleic acids, polysacharides) are accepted as conclusively detected. In this way it is prevented that areas of the impression which are detected in the optical mode and which originate, for example, from inorganic contamination (dust etc.) or, for example, from transferred components from the medium or agar, erroneously contribute to the result. In the sense of one process variant, the resulting spectra can, if desired, also be used immediately or at a later time with a view to identifying the microorganisms, by comparison with a reference spectra database in the desired spectral region(s), which may also be very small, in accordance with the published principles of the procedure (see above). A number of further method modifications are possible in order to achieve, if desired, greater independence of the method from human intervention in the procedure, as described above in principle. Thus, for example, the transfer steps provided (that is to say a) application of the sample to the culture plate, b) transfer of the inocculated culture plate to an incubator, c) stamp impression for transfer of the microcolonies from the culture carrier to the optical sample carrier, d) if appropriate transfer of the sample carrier to the sample stage of the IR microscope and e) removal of the sample after measurement has been carried out) can easily be mechanized and/or automated with the aid of customary mechanical and/or electronic components. A fully automated procedure going beyond this can be achieved by adding an image processing system consisting of a camera flange-mounted on the IR microscope, an electronically controlled stage with X and Y movements as the microscope stage, an electronically controlled unit for switching between the optical and the IR microscope mode of the microscope, a control unit or computing unit (for example personal computer with appropriate interfaces or other computer systems) and one or more appropriate computation programs. Appropriately, the computer and control unit including computation programs can be integrated in the computer/control unit which is present from the outset and serves to control the FT-IR equipment including the IR microscope.

A fully automated procedure is then as follows: after transfer of the sample carrier, containing the microcolony impressions, to the X–Y stage of the IR microscope, an image of the carrier can be recorded by the camera in the optical mode of the microscope and supplied to the computer/control unit in digital form (in at least 256×256 pixels, for example 64 grey scales). The X–Y positions of possible microcolony impressions can be determined in the computer/control unit using a sub-program, by evaluation of the digital grey scale distribution of the image, for example using a peak search algorithm. The control unit can then set a suitable aperture (diameter for example 30–80 μm), carry out positioning to the location coordinates of the first suspected microcolony impression and record the infra-red spectrum at this location. This operation can be repeated until it has been completed for all previously determined X–Y positions. The control unit can then call up a further sub-program which checks all spectra recorded in this way for compatibility with microorganism spectra. This can be achieved, for example, via a simple cross-correlation, if appropriate with prior filtering, of the spectra with reference spectra of microorganisms, since for each individual or combined spectral region, for a given filter method, a threshold value of the correlation coefficient between microorganism spectra exists below which the suspected microcolony is identified as inorganic or organic contamination of the sample carrier. With this procedure a reference database of 5–20 typical microorganism spectra (for example Staphylococci, Streptococci, Clostridia, Pseudomonads, Entero-bacteria, Salmonella, Legionella and Bacilli) suffices for reliable discrimination between microorganisms and contamination. Of course, peak tables or, for example, evaluation using known methods of multi-variance statistics can also be used for special applications. The number of microorganisms present in the sample can then be calculated, for example as germ count/ml of sample, by the control/computer unit from the number of positions confirmed as microcolony impressions, if appropriate taking account of corresponding dilution factors, and can be given as output. With the aid of the control and computer unit it is, of course, also possible, if desired, with appropriate programming, to carry out a subsequent identification of the microorganisms detected, by comparison with a reference database which consists of reference spectra measured under the same conditions. The parts of the program required are based on algorithms well known to those skilled in the art and can be written from scratch or taken from a multiplicity of generally obtainable program systems (a program which has been successfully used in this context is, for example, the IMAGIC program, cf. M. van Heel, W. Keegstra, Ultramicroscopy 7, 113, 1981).

Overall, the new method for the detection of microorganisms permits, in the manner described, a rapid qualitative and quantitative detection of microorganisms, in principle of all types, with the further advantage of the additional identification using the same basic equipment within a period of about 4–10 hours or less after submission of the sample, without prior pure culture, this period being determined virtually in total by the incubation time necessary to obtain microcolonies, since the further process steps take only minutes to less than 1 hour if the method is carried out in a suitable manner.

EXAMPLE 1

Figures 1A, 1B:
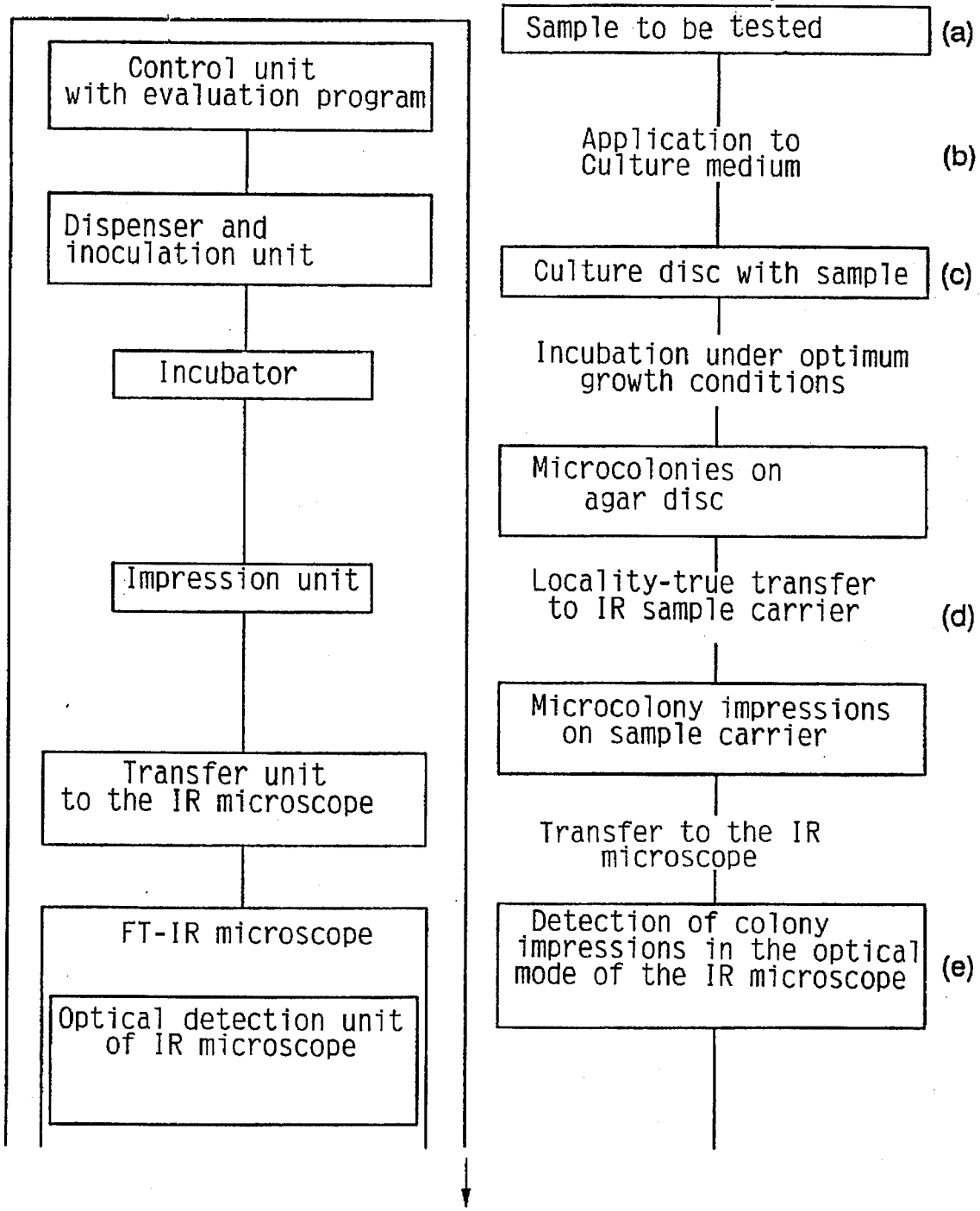
FIGS. 1a and 1b collectively depict a flow chart showing, in the right-hand column, the general overall procedure for the rapid detection of microorganisms, and in the left-hand column, the subcomponents of the apparatus in the situation of an automated procedure.
Figures 1A, 1B:
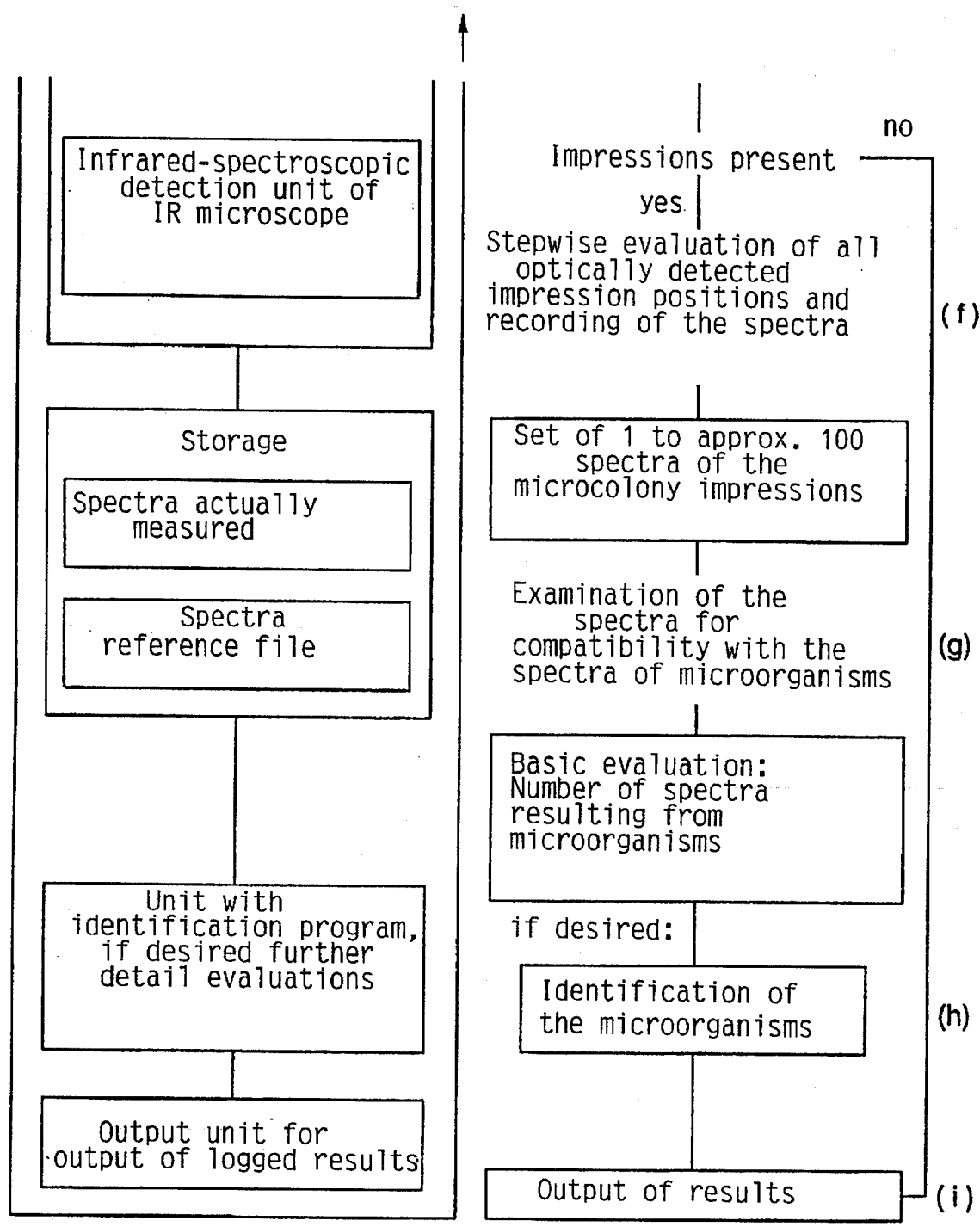
Figure 2:
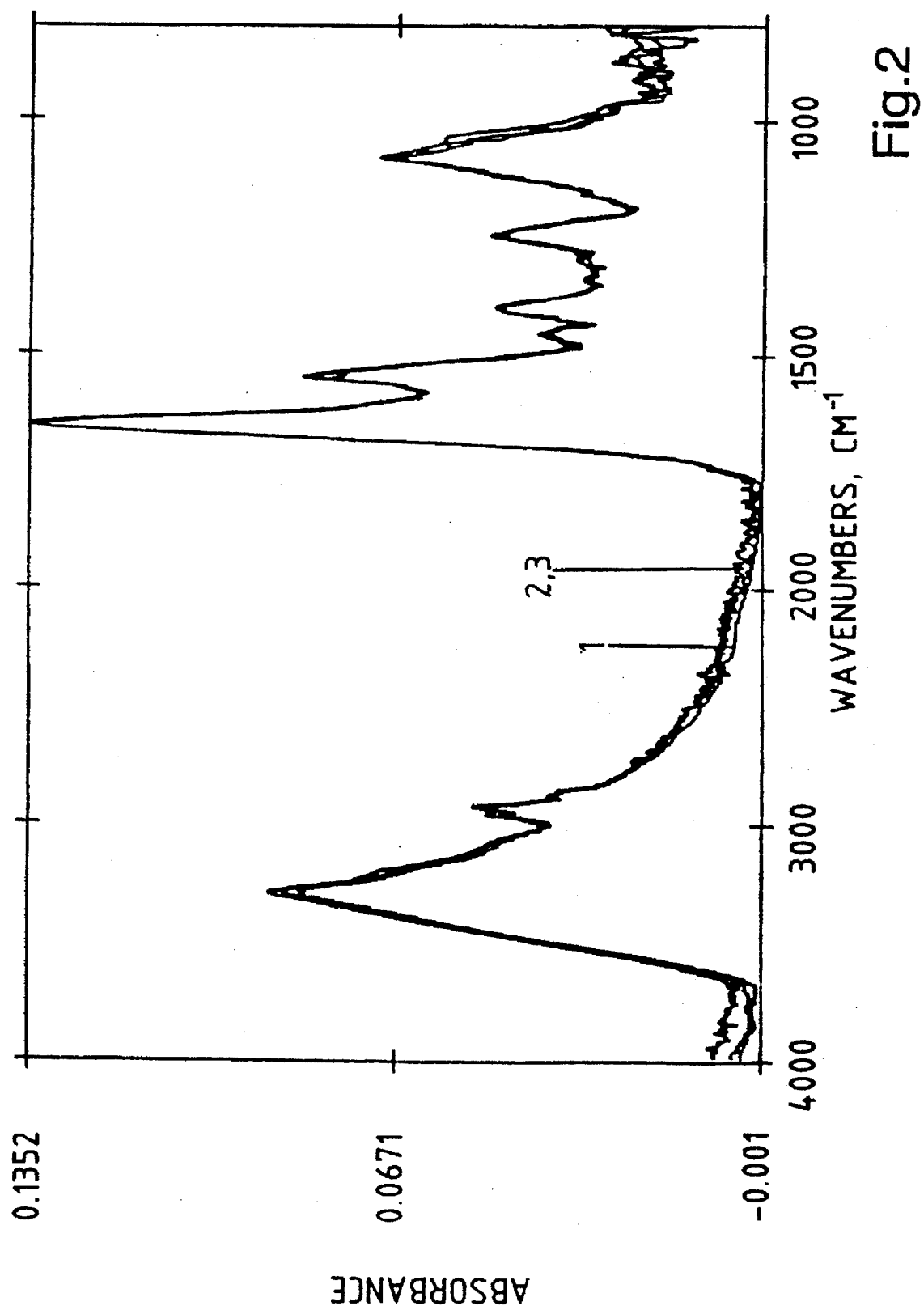
FIG. 2 depicts spectral plots recorded in the optical mode of an IR microscope of $10^4$, $10^3$ and $10^2$ *Klebsiella pneumoniae* cells grown on an agar plate and subsequently transferred to a sample carrier.

This Example 1, in conjunction with FIG. 2, is intended to verify the exceptional sensitivity of the new method, without describing the entire procedure.

FIG. 2 shows three spectra obtained in the following way using a A 560 infra-red microscope from Bruker, Karlsruhe, coupled with an IFS 48 FT-IR spectrometer from the same company:

100 μl of a $10^3$ germ/ml culture of *Klebsiella pneuminiae*, ATCC 13882 in peptone water was coated onto a peptone agar plate and incubated for 8 hours at 37° C. (about 24 generation times). The impression of the bacteria was obtained by carefully laying on and removing again a polished $BaF_2$ sample carrier 40 mm in diameter and 3 mm thick. The bacterial film which is transferred in this way and as a rule (especially in the case of relatively short incubation times) consists of 1–3 layers of bacteria, dries within a few seconds under ambient conditions without using vacuum or dessicants. Inspection of the sample carrier in the optical mode of the IR microscope (15× lens, Casse-granian, 20× eyepiece) gave an extended, thin 1–3 layer bacterial film over virtually the entire sample carrier surface. By selection of suitable circular apertures it was achieved that in each case about $10^4$ (spectral plot 1 in FIG. 2, 8 μm diameter aperture), about $10^3$ (spectral plot 2, 40 μm diameter aperture) and about $10^2$ (spectral plot 3, 20 μm diameter aperture) microorganisms contribute to the spectrum. All spectra were recorded in transmission. 512 scans were accumulated at a spectral resolution of 8 $cm^{-1}$. Inspection of FIG. 2 clearly shows that spectral signals clearly detectable as microorganism spectra can already be obtained, in this case in the wavenumber range of about 4000-900, with about $10^2$ microorganisms (corresponding to less than 0.1 ng of substance). Because of the relatively high noise content (cf. spectral plot 3 in FIG. 2), however, working with at least about $10^3$ microorganisms is to be preferred if an identification, for example species identification, which is as exact as possible is to follow the detection using the same set of data. It can be seen from this typical measurement example that the incubation time of the sample on the culture plate should be at least about 6 to 12 generation times in order to allow a microcolony of about 200–4000 organisms to form from each microorganism isolated by application in appropriate dilution to the culture plate. Thus, for example, a lower limit for the incubation period of less than 4 hours results for Enterobacteriaceae (typical generation time on customary media about 20 minutes) and of about 5 hours for Staphylococci (generation time on customary media about 30 minutes), etc..

EXAMPLE 2

This example shows a typical procedure in the case of an experiment carried out manually using as an example an aqueous sample to which $10^3$ cells/ml of *Staphylococcus aureus*, Pelzer strain, were artificially added. 100 μl of this sample were applied to a peptone agar plate (100 mm diameter) and distributed with the aid of a Drigalski spatula. After an incubation time of 8 hours at 37° C. in an incubator, the microcolonies (not yet discernible with the naked eye) were transferred locality-true to a 60 mm BaF$_2$ plate in the manner described in Example 1 (stamp impression).

Figure 3:
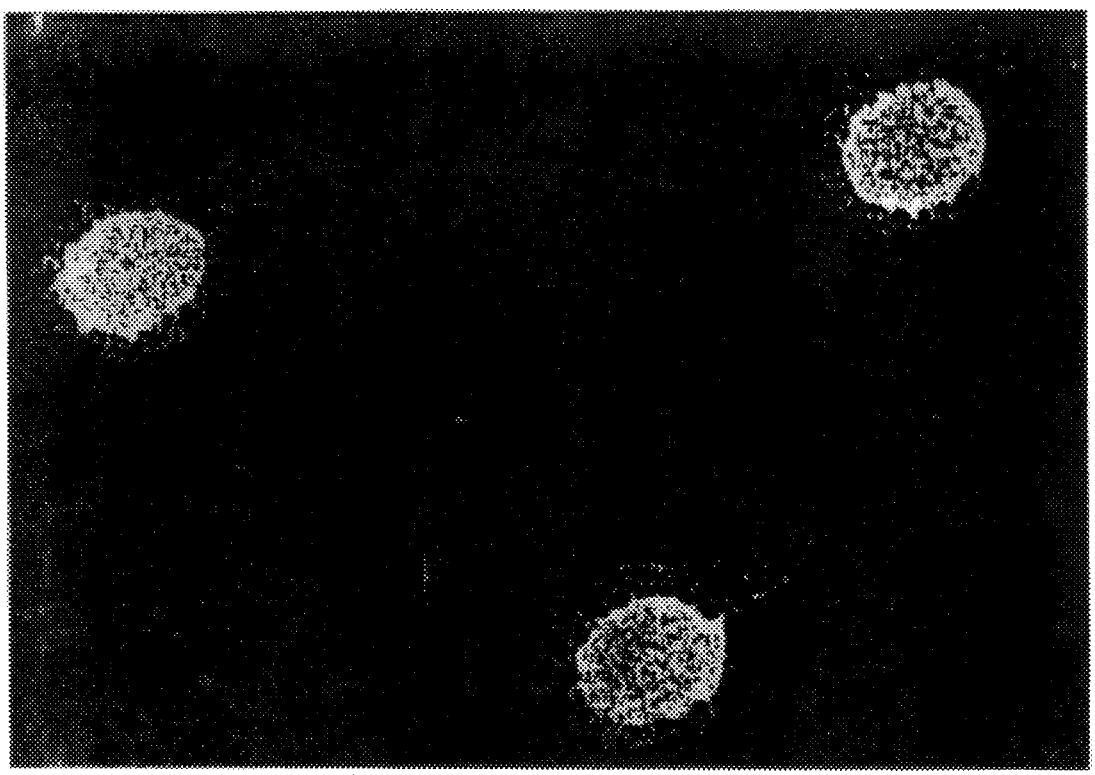
FIG. 3 is a photograph of a section of a sample carrier which contains three transferred *Staphylococcus aureus* microcolonies obtained by applying the sample carrier to an agar plate containing the microcolonies.
Figure 4:
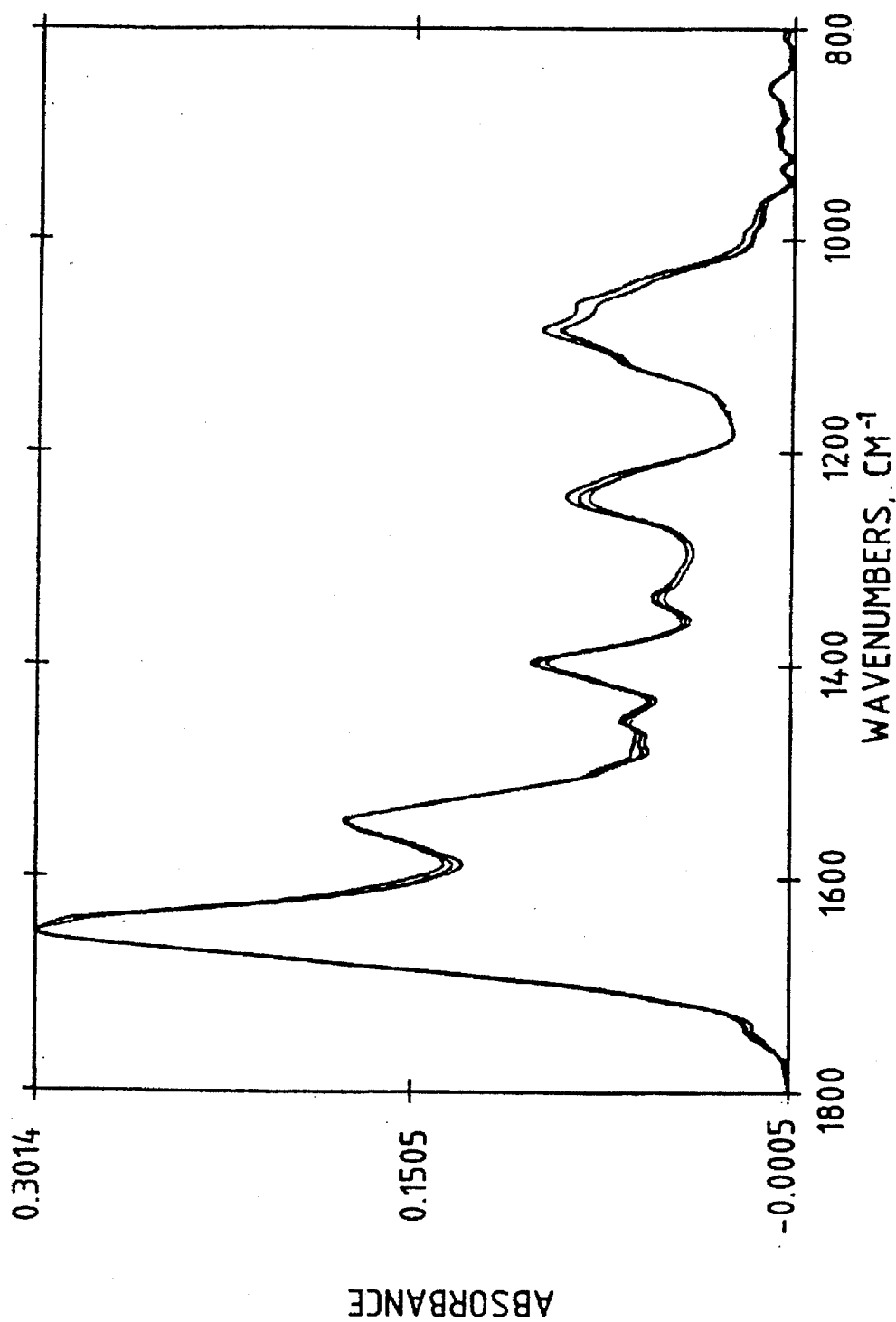
FIG. 4 depicts spectral plots, recorded in the optical mode of an IR microscope, for the three transferred Staphylococcus microcolonies shown in FIG. 3.

FIG. 3 shows a photograph (magnification 250) of a section of the sample carrier. The spectra obtained in the region between 1800 and 800 cm$^{-1}$ for the three microcolony impressions shown in FIG. 3 are shown in FIG. 4. Visual comparison of the three spectra already shows the excellent reproducibility of the method in detecting different microcolonies of the same microorganism. For quantitative confirmation, the so-called differentiation index D (D=(1−α)·1000, α=Pearson correlation coefficient) was determined by cross-correlation. In the case of the measurements shown here and also of measurements carried out analogously for further species a D value of ≈8 was obtained, incorporating measurements on independently prepared samples which were prepared at different times on agar plates of different batches of the same nutrient medium. Thus, the D value of about 8 (corresponding to a correlation coefficient of 0.992!) defines the surprisingly good level of reproduction of the method and provides the threshold value for differentiation of different microorganisms in the case where subsequent differentiation or identification of the detected microorganisms is desired. In the example described, 17 microcolony impressions were detected on the carrier plate by means of their infra-red spectrum. Taking account of the amount of sample employed (100 µl) and of the ratio of the surface area of the agar plate to the surface area of the sample carrier (6.26:1), a detected germ count of 1.06×10$^3$, which is in excellent agreement with the value employed, is calculated from this value.

EXAMPLE 3

This example illustrates the procedure for identification of the microorganisms found, following their detection: 100 µl of a water sample containing *Staphylococcus aureus*, *Staphylococcus xylosus* and *Klebsiella pneumonias*, in each case in an amount of 10$^3$ germs per ml, were applied as in Example 2 to a peptone/agar plate and after an incubation time of 8 hours applied to the same sample carrier as described in Example 2, using the identical stamp technique.

Figure 5:
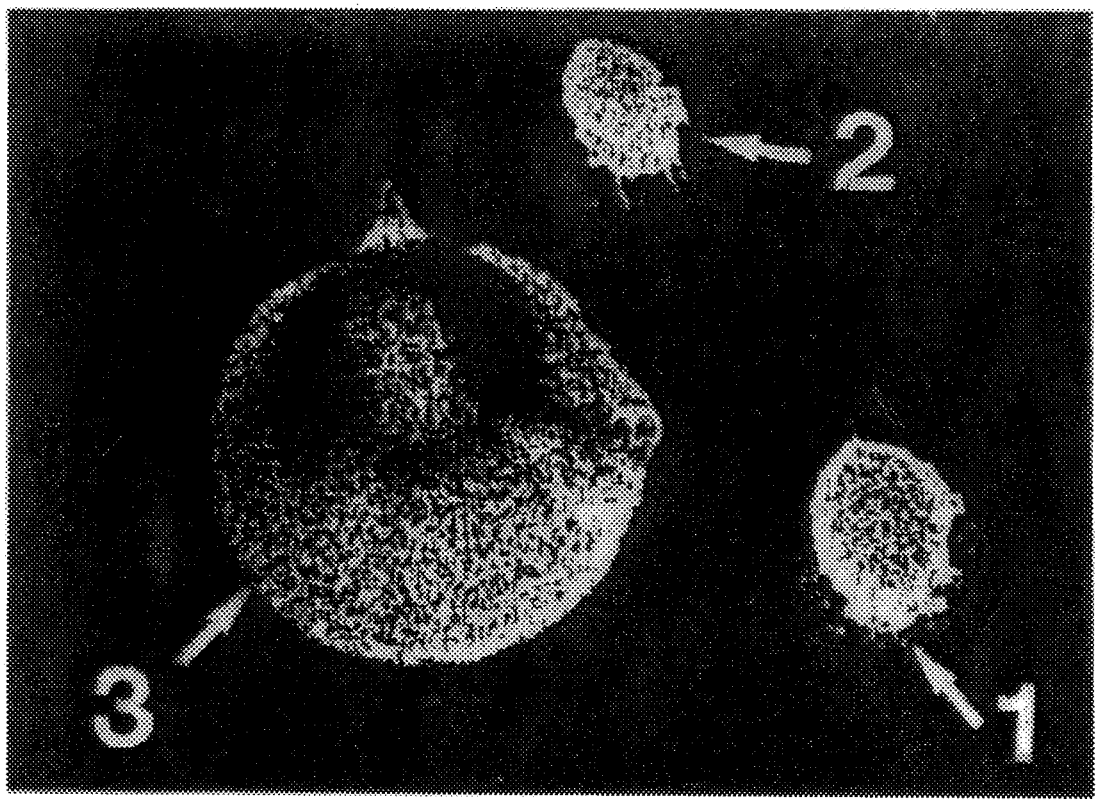
FIG. 5 is a photograph of a section of a sample carrier containing a transferred *Staphylococcus aureus* microcolony, a transferred *Staphylococcus xylosus* microcolony and a transferred *Klebsiella pneumoniae* microcolony obtained by applying the sample carrier to an agar plate containing the microcolonies.
Figure 6:
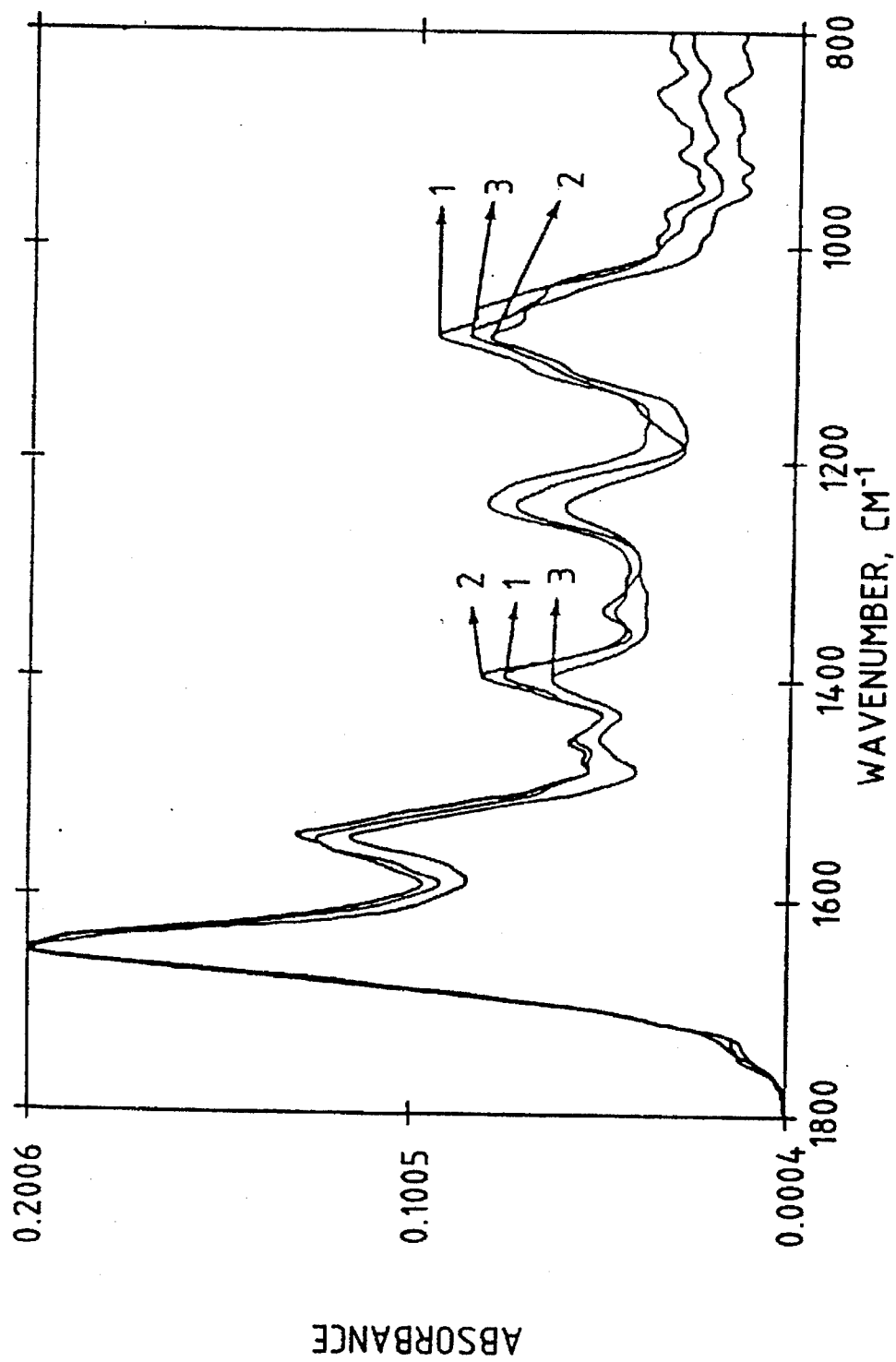
FIG. 6 depicts spectral plots recorded in the infra-red mode of an IR microscope for the three transferred *Staphylococcus aureau*, *Staphylococcus xylosus* and *Klebsiella pneumoniae* microcolonies shown in FIG. 5.

FIG. 3 shows a section of the sample carrier, with a magnification of 250. Because of the locality-true and thus area-true transfer of the microcolonies, observation in the optical mode of the microscope already indicates, even to an operator with only little training in bacteriology, the participation of several organisms, since the different microcolony sizes, as can be seen from FIG. 4, already indicate three different microorganisms. Under higher magnification, the morphology of the individual bacteria (for example cocci or rods) can also be taken into account. However, this represents only a possible additional aid for the person carrying Out the experiment, since in the procedure the detection is effected by recording of the corresponding infra-red spectra. FIG. 6 shows the spectra obtained in the infra-red mode of the FT-IR microscope for the microcolony impressions designated 1, 2 and 3 in FIG. 5. Via the characteristic sample curve, all spectra indicate the presence of microorganisms. Comparison of the spectral plots shown in FIG. 6 with those from a reference database of 100 spectra of bacteria of 40 different species gave a species-accurate identification for all microcolony impressions on the basis of the lowest D values, calculated from the first differentiations of the spectra in the wavenumber range of 1500-900 cm$^{-1}$.

EXAMPLES AND REMARKS WITH REGARD TO FIG. 1

(a) For example urine, liquor, blood, foodstuffs, water, etc., if necessary after appropriate preparation and dilution (b) For example agar plate with added blood, peptone or the like, if appropriate selective or elective medium (c) For example 20°–40° Celsius, pH 4–9, for, for example, 4–10 hours or about 8–20 generation times of the microorganisms (d) For example stamp impression on ZnSe, BaF$_2$ discs, polymer film aluminium platelets, polished steel platelets, etc.

(e) For example manual, visual or automated scanning of the sample carrier, recording and if appropriate electronic storage of impression position coordinates, if appropriate using image processing techniques which provide information with respect to number, position and size of the colony impressions (f) For example series, manual or automatically controlled movement to the impression coordinates determined in the previous step, selection of a suitable aperture in the range of about 10–200 µm and recording of the spectra in the wavenumber region of, for example, 5000-500 in the mid infra-red (g) For example optical evaluation of the spectra by the person carrying out the experiment, calculation of correlation coefficients to reference spectra, multivariance analysis of the spectra, etc.

(h) If appropriate, identification by comparison with reference data (i) Taking account of sample dilution etc., if appropriate, additional results such as identification, colony shape, etc.

What is claimed is:

1. A method for rapid detection of microorganisms in a sample, the method comprising the steps of:
    a) applying the sample to a surface of an essentially solid culture carrier in a dilution which enables growth of microorganisms in locally separate microcolonies,
    b) incubating the sample of step a) to form locally separated microcolonies of 50 to 4,000 microorganism cells,
    c) transferring a region of the surface of the culture carrier to a surface of an optical carrier stamp without changing relative geometrical locations of the transferred microcolonies with respect to each other, the stamp surface being at least one of transparent and reflective in a desired spectral region,
    d) positioning the optical carrier stamp under an infra-red microscope,
    e) detecting the transferred microcolonies using an optical mode of the infra-red microscope,
    f) determining relative geometrical locations of the transferred microcolonies on the stamp,
    g) sequentially recording IR spectra of the transferred microcolonies, and
    h) comparing the recorded IR spectra with each other and with a spectra reference file to rapidly detect microorganisms.

2. A method for the rapid identification of microorganisms in a sample, comprising the steps of:
    a) applying the sample to a surface of an essentially solid culture carrier, in a dilution which enables growth of microorganisms in locally separate microcolonies, b) incubating the sample of step a) for at least 6 generation times to form locally separated microcolonies of 50 to 4,000 microorganism cells, c) transferring a region of the surface of the culture carrier having microcolonies to a surface of an optical carrier stamp without changing relative geometrical locations of the transferred microcolonies with respect to each other, the stamp surface being at least one of transparent and reflective in a desired spectral region, d) positioning the optical carrier stamp under an infra-red microscope, e) detecting the transferred microcolonies using an optical mode of the infra-red microscope, f) determining the relative geometrical locations of the transferred microcolonies on the stamp, g) sequentially recording IR spectra of the transferred microcolonies using the infra-red microscope in at least one of a transmission and a reflection mode, the microscope having apertures in a diameter range of 10–200 µm, h) comparing the recorded IR spectra with each other and with a spectra reference file to rapidly identify the microorganisms.

* * * * *